(12) United States Patent
Glatt et al.

(10) Patent No.: US 6,736,844 B1
(45) Date of Patent: May 18, 2004

(54) HELICAL STENT AND METHOD FOR MAKING SAME

(76) Inventors: Bernard Glatt, 5 Avenue Mozart, 75016 Paris (FR); Bernard Chevalier, 22 rue Albert Molinier, 95140 Groslay (FR); Truhierry Royer, 1 rue de Tretaigne, 75018 Paris (FR); Philippe Guyon, 65 rue de la Republique, 92800 Puteaux (FR); Bruno LeCointe, 17 Cote de la Jonchere, 92500 Rueil Malmaison (FR); Dominique Roy, 2 Avenue de la Concorde, 78320 Le Mesnil Saint Denis (FR); Gilles Ascher, 192 Avenue Victor Hugo, 75116 Paris (FR)

( * ) Notice: Subject to any disclaimer, the term of this patent is extended or adjusted under 35 U.S.C. 154(b) by 0 days.

(21) Appl. No.: 09/381,352
(22) PCT Filed: Mar. 3, 1998
(86) PCT No.: PCT/FR98/00409
§ 371 (c)(1),
(2), (4) Date: Nov. 9, 1999
(87) PCT Pub. No.: WO98/38945
PCT Pub. Date: Sep. 11, 1998

(65) Prior Publication Data
(65)

(30) Foreign Application Priority Data
Mar. 4, 1997 (FR) .............................. 97 02526

(51) Int. Cl.$^7$ ................................................ A61F 2/06
(52) U.S. Cl. ...................................... 623/1.22; 623/1.15
(58) Field of Search ............................... 623/1.15, 1.16, 623/1.22, 1.51, 1.54, 1.5, 1.53, 1.32

(56) References Cited

U.S. PATENT DOCUMENTS

| | | | | |
|---|---|---|---|---|
| 4,760,849 A | * | 8/1988 | Kropf | 606/191 |
| 5,133,732 A | * | 7/1992 | Wiktor | 606/195 |
| 5,314,472 A | | 5/1994 | Fontaine | |
| 5,607,445 A | * | 3/1997 | Summers | 623/1.22 |
| D380,266 S | * | 6/1997 | Boatman et al. | D24/155 |
| 5,643,339 A | * | 7/1997 | Kavteladze et al. | 623/1.22 |
| 5,755,771 A | | 5/1998 | Penn et al. | 623/1 |
| 5,810,872 A | * | 9/1998 | Kanesaka et al. | 606/198 |
| 5,906,640 A | * | 5/1999 | Penn et al. | 623/1.15 |
| 5,925,061 A | * | 7/1999 | Ogi et al. | 606/198 |
| 6,007,574 A | * | 12/1999 | Pulnev et al. | 623/1.15 |
| 6,013,854 A | * | 1/2000 | Moriuchi | 606/198 X |

FOREIGN PATENT DOCUMENTS

| | | |
|---|---|---|
| EP | 0540290 | 5/1993 |
| FR | 2 391 709 | 11/1976 |
| GB | 1 565 828 | 4/1980 |
| WO | 9531945 A | 11/1995 |
| WO | 9603092 A | 2/1996 |

* cited by examiner

Primary Examiner—Bruce Snow
Assistant Examiner—Brian E. Pellegrino
(74) Attorney, Agent, or Firm—Dennison, Schultz, Dougherty & MacDonald

(57) ABSTRACT

A stent having a first filamentary element (20) with a proximal end portion and a distal end portion, and being spirally coiled in at least its central portion, and a second filamentary element (30) spirally coiled along its central portion and overlapping the first filamentary element to form a double helix is disclosed along with a method for forming such a stent. At least one end portion of the first filamentary element is ring-shaped to provide increased radial support at that end of the stent.

23 Claims, 9 Drawing Sheets

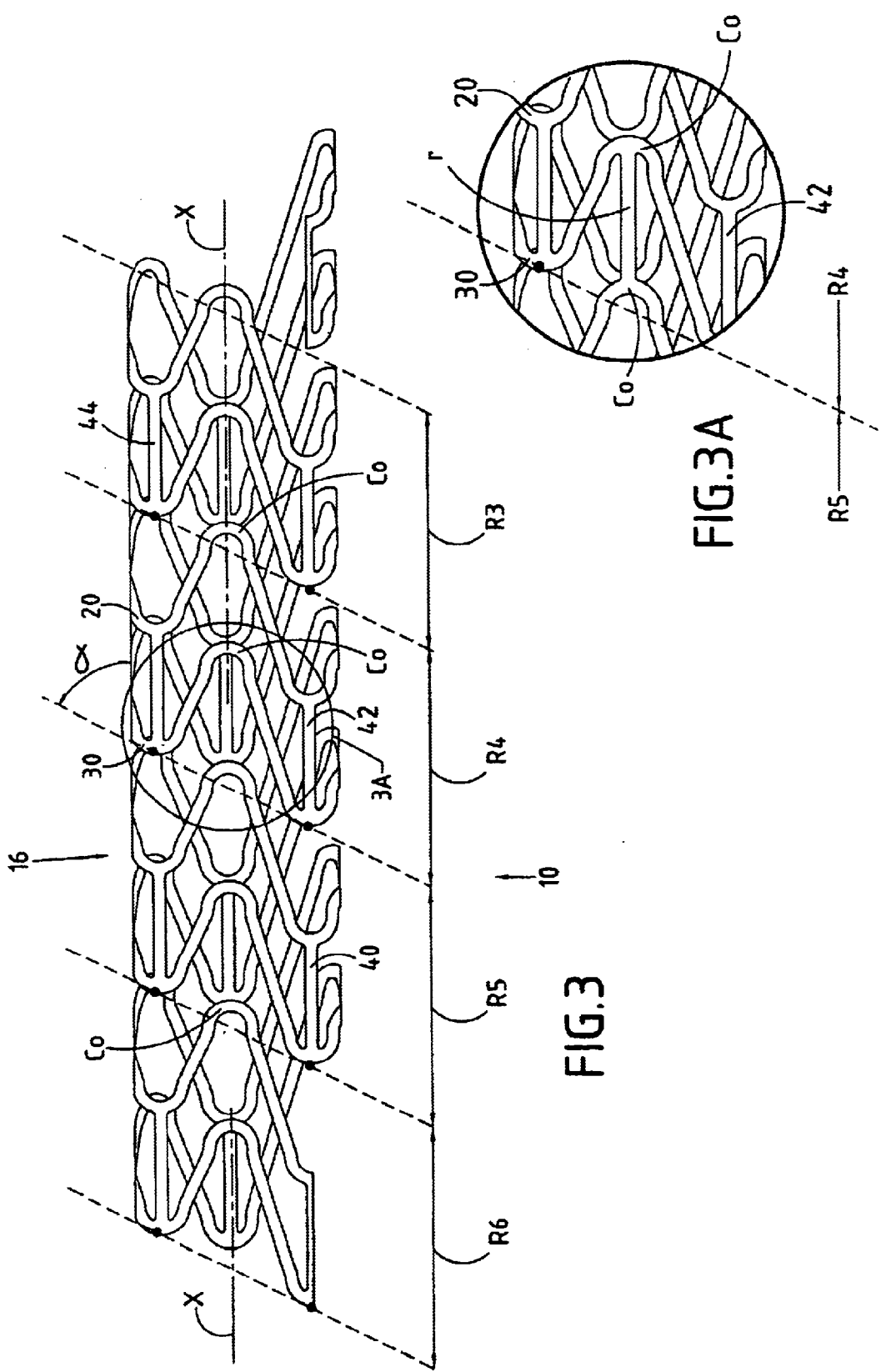

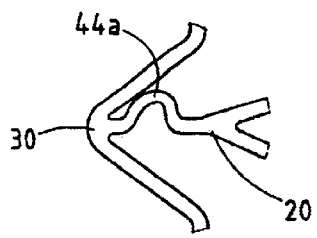
FIG.4A
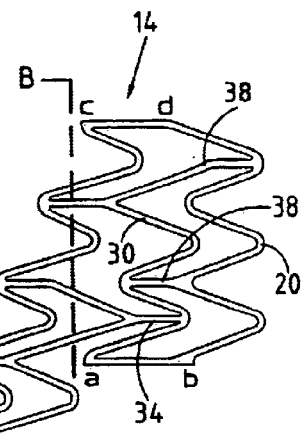
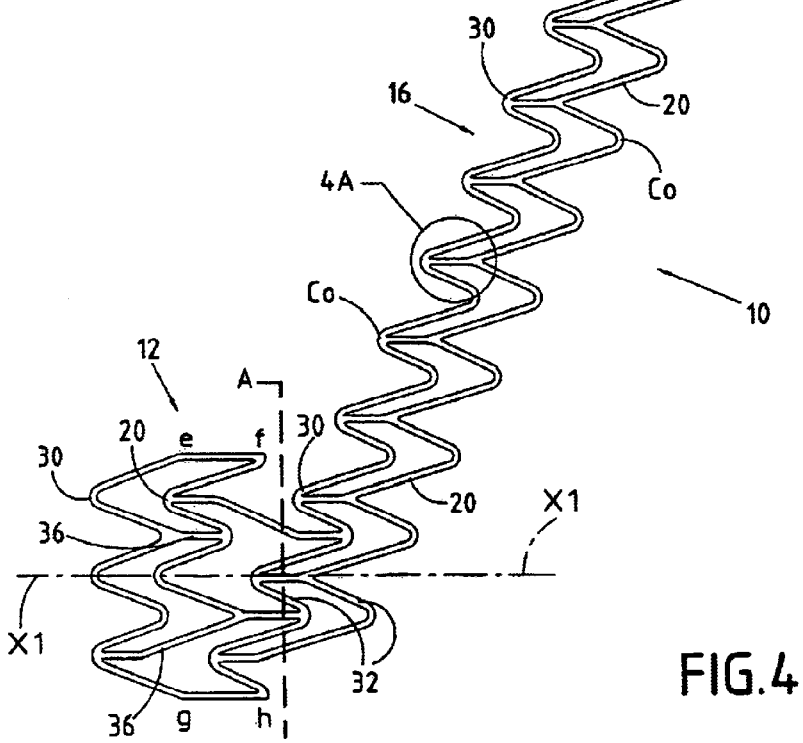
FIG.4

HELICAL STENT AND METHOD FOR MAKING SAME

The invention essentially relates to a spiral stent forming device as well as to a method of making it.

It is known that devices forming endoprotheses, also known as "stents", enable treating narrowing of various canals of the human anatomy, such as an artery, and to keep them open.

Several types of stents exist: tubular, network, filamentary, balloon-expandable or self-expandable stents.

For example, the document U.S. Pat. No. 5,578,149 as well as U.S. Pat. No. 5,591,230 describe a stent which is formed by a filamentary element coiled in a spiral and having bends which define a zigzag structure, enabling a significant radial expansion with a low shortening of the length of the stent.

The fault of these stents is that they have a weak shoring up strength at the ends and poor covering power at the ends.

Furthermore, it is also known from U.S. Pat. No. 4,553,545, of various embodiments of a stent which is formed by a filamentary element coiled in a spiral. With reference to FIG. 10 of this patent, a risk is presented of shifting or of crushing or of unwinding of the stent during a radial expansion, and this is also explained in column 7, lines 56 et seq. In order to remedy this, this patent proposes rigidifying the turns by a rigidifying element, see FIGS. 11 to 16. A stent of ladder construction is then proposed in FIGS. 22 and 23, and notably with reference to FIG. 23, a stent is formed by a double helix spiral which is joined by transversal elements 82. It is indicated that this structure enables improving the stability during a radial expansion (column 12, lines 45 to 66).

The fault of these stents is that they have a weak shoring up strength at the ends and poor covering power at the ends.

Further, if an obstacle is encountered during the insertion of the stent forming device, due to the absence of hold of the spiral at the ends, a subsidence of the spiral can be produced in some cases.

It is further known from the document WO-A-96/03092, of a stent forming device which is constituted by a filamentary element coiled in a ring-like fashion, which is constituted of a certain number of rings joined together by bent binding elements 22, the ring-like portions being also bent so as to form a zigzag structure. This device has a good shoring up strength during a radial expansion. This device has a certain flexibility by virtue of the presence of joints 22 comprising bends 20, between the ring-like elements 11, but this flexibility is essentially lost after expansion and gives rise to constraints on the canals, and in particular the arteries. It will be observed that the structure described in this document provides, after unfolding, a network or cellular system, as is clearly represented in FIG. 4, which favors the shoring up, but limits the flexibility and the shapability to the canal, and this constitutes a significant requirement.

The current limits of these known stent forming devices remain:

a) the rigidity of certain stents, which can compromise an access to certain lesions, the upstream of which is winding. This rigidity becomes a drawback insofar as stent forming devices of longer length are more and more sought after, at the same time as the stent forming devices being capable of making winding accesses and for which a greater flexibility is sought. The stent forming device described in the document WO-A-96/03092 has a flexibility which is improved with respect to the prior art devices, but which is still judged to be insufficient, notably in the case of long lengths, i.e. beyond 20 mm, which is the current tendency.

b) the constraints given rise to on the artery upstream and downstream from the stent resulting from a drawing out phenomenon by rigidification of the canal after unfolding of the stent. This can give rise to complications during the intervention of tissue reactions leading to a recurrent narrowing of the canal mentioned above. This leads to an insufficient shapability to the canal, and notably to the ends, giving rise to constraints which are not very satisfactory to said ends, and this in particular is the case in the document WO-A-96/03092.

c) the difficulty of getting over the stent when it is implanted straddling over a bifurcation and that the branch must be treated as well. In particular, it may be necessary to pass a balloon or a stent on balloon through the structure of the first stent. This also is in particular the case in the document WO-A-96/03092.

d) Certain stents lack radial strength, called shoring up strength, in particular at the ends, and this can be important for shoring up the origin (ostium) of a canal such as an artery, which is in general very elastic. This is in particular the case of stent forming devices described in the documents U.S. Pat. No. 5,578,149, U.S. Pat. No. 5,591,230, and U.S. Pat. No. 4,553,545. The shoring up strength of the whole of the stent is also very important when lesions exert a strong resistance to the dilatation, as is the case of calcified lesions or lesions having strong elastic recoil.

e) Certain filamentary type stents deform longitudinally during a blockage of the progression during the access to a lesion due to a lack of hold of the structure. This is in particular the case of the stent forming devices described in the documents U.S. Pat. No. 5,578,149, U.S. Pat. No. 5,591,230, and U.S. Pat. No. 4,553,545.

Thus, in the known prior art devices, these are of a design which is either entirely spiral, or entirely ring-like. Further, for certain ring-like type stents, these can be produced in a network, as in the case of the document WO 96/03092.

Thus, the main aim of the present invention is to solve the novel technical problem consisting of providing a solution, which consists of a novel stent forming device, which has simultaneously the following properties:

a) a very good flexibility, b) a lateral crossing capacity from the inside of the stent by another stent or a balloon device, c) a very good shapability in the longitudinal sense, so as not to modify the curvature of the canal in which the stent must be implanted, in the longitudinal sense, d) a very good radial strength so as to completely fill its role of shoring up the canal in which the stent must be implanted, e) a very good crossing capacity enabling a longitudinal passage by another device such as a balloon or another stent, optionally also on a balloon, f) a very good capacity to keep in place in unfolded position, g) a very good capacity of shoring up and of ring-like covering of the ends enabling a complete covering without overrunning, which is particularly important notably in the medical field at the level of ostia.

h) an expansion essentially without shortening of the length of the stent, and this even for stents of long lengths, namely greater than about 20 mm.

Thus, a further main aim of the invention is to provide a solution to the novel technical problem above, according to a particularly simple design which is relatively inexpensive and which can be used on an industrial and medical scale.

Thus, according to a first aspect, the present invention provides a stent forming device comprising a first filamentary element coiled spirally at least in its central portion, and a proximal end portion and a distal end portion, characterized in that it comprises a second filamentary element coiled spirally at least in its central portion, said first and second elements thus defining a double helix structure, and in that at least one, preferably both, end portion(s) is (are) produced with at least one said filamentary element coiled in substantially ring-like fashion. This device enables thus reinforcing notably the maintenance of the structure in place as well as ensuring a complete covering without running over, particularly at the level of the ostium.

According to an advantageous embodiment of the invention, the device comprises end portions defining respectively a proximal end edge and a distal end edge of the device, said end portions being produced with said first and second filamentary elements coiled in substantially ring-like fashion and joined onto said central portion composed of the first element and of the second filamentary element mentioned above in a double helix.

According to another advantageous embodiment of the invention, said first element and said second filamentary elements forming a double helix structure mentioned above are bent so as to produce a zigzag form, in producing here a spiral zigzag form.

According to a variant enabling a good transversal crossing, the central portion in a double helix comprises at least 3 bends defining at least 3 vertices per 360° turn.

According to a particular embodiment of the invention, the end portions produce a general ring-like form which is joined directly or via at least one joint to the central portion in a double helix.

According to another particular embodiment of the invention, the proximal edge and the distal edge of the ends are comprised in a plane of circular cross-section, the center of which substantially coincides with the longitudinal axis which is defined by at least the central portion mentioned above in a double helix.

According to an advantageous variant, the proximal edge and the distal edge are comprised in a plane of circular cross-section which is substantially perpendicular to the longitudinal axis which is defined by at least the central portion mentioned above in a double helix.

According to another variant of the invention, the proximal edge and the distal edge are comprised in a plane of circular cross-section forming an acute angle with the longitudinal axis of the device, of between less than 90° and at least 60°, preferably between less than 90° and at least 70°.

According to another advantageous embodiment of the invention, said first filamentary element and second filamentary element are joined together by at least some linking arms spaced out along said central portion.

According to a variant, the double helix being composed of successive 360° turns, at least some turns comprise at least one linking arm between the first element and the second element. Advantageously, each 360° turn comprises at least one linking arm.

According to another variant, each turn comprises at least two linking arms.

According to yet another particularly advantageous variant, some linking arms or each linking arm can be itself bent in having one or more bends so as to improve the flexibility enabling also improving the ability to be shaped to the canal.

According to yet another advantageous embodiment of the invention, the linking arms mentioned above produce a size which is sufficient to enable a sufficient space to be defined between the first and the second spiral elements mentioned above, for the passage of a tool in an adjacent canal to the canal in which the stent forming device has been disposed.

Advantageously, the length of the linking arm is of the order of at least 0.5 mm. Advantageously, the length of the linking arm will be of between about 0.5 mm and 5 mm.

According to yet another variant, the central portion comprises at least one reinforcing joint r joining in two vertices CO of two successive spiral turns. Advantageously, these reinforcing joints r can be of a number of one or more per turn, advantageously in a staggered manner with respect to the linking arms.

According to another embodiment of the invention, the straight cross-section of at least one or both said first and second filamentary elements mentioned above is selected from the group consisting of a straight circular section, of a straight polygonal cross-section such as square, rectangular, pentagonal, hexagonal or octagonal, of a straight polygonal cross-section having rounded edges, such as square having rounded edges or rectangular having rounded edges, or of a straight oval cross-section.

According to a particular embodiment, the size of the straight cross-section is related directly to the size of the straight cross-section of the canal in which the stent forming device must be inserted. Furthermore, generally, the diameter of said first element or of said second element, or of both, is of between about one hundredth and about one tenth of the diameter of the straight cross-section defined by the ring-like end portion of the stent forming device, in its initial ready-to-use machining form.

Advantageously, the diameter of the linking arm will be substantially equal to the diameter of said filamentary element, advantageously the shape of the linking arm is also substantially identical to that of the filamentary element.

According to an embodiment, said first filamentary element or the second filamentary element, or both, define a spiral having an inclination with respect to the longitudinal axis, at least in the central portion mentioned above, of between about 45° and about 80°, advantageously of between about 50° and 70°, and currently preferably of about 60°.

According to yet another embodiment of the invention, each bend of the filamentary element mentioned above has an acute angle which is defined by two successive portions of the filamentary element, of between about 20° and about 60°.

According to another advantageous embodiment of the invention, the stent forming device mentioned above is made as a monoblock, without soldering, from its proximal end to its distal end, and this simplifies its preparation and removes any risk of corrosion and rupture.

Within the context of the invention, any material which is compatible with an implantation into the body of a mammal, preferably man or an animal, can be used as material constituting the stent forming device. Such materials are generally constituted of a biocompatible material, particularly a biodegradable polymer or a metal such as a stainless steel of medical quality, a material having of shape memory, for example a material based on an alloy of nickel and titanium. Materials of low elastic memory can be used which can undergo an irreversible plastic deformation in exerting a radial mechanical force from the inside out towards the exterior, as is well-known to the person skilled in the art.

According to a second aspect, the present invention also provides a method of making the stent forming device mentioned above, characterized in that it comprises cutting out a tubular element of full cylindrical surface in a way so as to define in this tubular element said central portion in a double helix, as well as the end portions mentioned above. Thus, it is possible to make the stent forming device as a monobloc and without soldering from one end to the other.

According to an advantageous embodiment, this cut-out is produced so as to define the precise embodiment sought in its initial form to be used as such.

According to a third aspect, the present invention also provides another method of making the stent forming device mentioned above, characterized in that a cut-out is made of a flat element or plate, so as to define the central portion mentioned above, which is intended to form a double helix by coiling on itself around a chuck of suitable shape, preferably having straight circular cross-section, said cut-out also producing the end portions mentioned above. Thus, it is possible to make the stent monoblock, but a soldering at each end is necessary after the coiling.

These cut-outs are produced with the aid of methods and devices which are well-known to the person skilled in the art. The person skilled in the art knows for example of machining techniques by laser, notably of the YAG or $CO_2$ type, or other, by electroerosion, or by a combination of the two; the electroerosion technique is also known as "etching". It is understood that when one starts off from a tube, the technique by laser ray consists in attacking the external surface of the tube by the laser beam so as to define the structure sought after, such as here the double helix structure in the central portion.

Further, when a thin plate is used, for example a rectangular plate, the laser beam machines in this plate the structure of the invention comprising the double helix in its central portion. Then, it will be sufficient to roll the structure obtained on a cylindrical chuck and finally to solder the edges of each of the ends.

Starting either from the tube, or from the thin plate, it N is also possible to use the technique of electroerosion or "etching" mentioned above.

According to a fourth aspect, the present invention provides another method of making the stent forming device mentioned above, characterized in that a cut-out is made from a flat element or plate, or from a tube, with the aid of a device for projecting a liquid under pressure, in particular water, of the Karcher® type.

According to a fifth aspect, the present invention also covers a method of preparation according to which said first filamentary element mentioned above of spiral shape and a second element independent filamentary of spiral shape are first of all made, and then said first element and second element are joined, according to a determined pitch, to end portions defining a proximal edge and a distal edge of the type described above within the context of the invention optionally with the presence of linking arms and/or of joints as described above.

By virtue of the invention, the technical problems set forth above are solved in a simple, relatively inexpensive manner which is usable on an industrial and medical scale.

Within the context of the present invention, it is observed that by a combination of essentially ring-like end(s) and spiral type central portion, the simultaneous obtaining of the whole of the requirements set forth above is lead to in an unexpected way for a person skilled in the art, namely, a very good flexibility, a very good capacity to lateral crossing from the inside, a very good shapability in the longitudinal sense, a very good radial strength, in particular at the ends, a very good shoring up capacity and ring-like covering at the ends enabling a complete covering without running over, an expansion which is essentially without shortening of he length of the stent, a very good capacity to crossing enabling a longitudinal passage by another device, such as a balloon, or another stent, optionally also on-balloon, a very good capacity of maintenance in the unfolded position combined with a very good drawing out capacity, even in the spiral central portion, and this even for stent forming devices of long lengths, i.e. of lengths longer than about 20 mm, and for sizes which can be greater than 50 mm.

Further, the invention, by combination of a spiral central portion, preferably a zigzag, with substantially ring-like ends, an easy setting is allowed on a positioning device, notably of the balloon type, and this was not allowed by the prior art devices of the spiral type, such as described in the U.S. Pat. No. 4,553,545.

The invention is further applicable to self-expandable devices or to non-self-expandable devices.

Other aims, characteristics and advantages of the invention will appear clearly in the light of the following explanatory description made with reference to the annexed drawings, which represent several currently preferred embodiments of the invention, which are given simply as an illustration, and which will in no way limit the scope of the invention.

In the Figures:

FIG. 3 represents an enlargement of the central portion of the embodiment of FIG. 1;

FIG. 3a represents a modification of the central portion of the embodiment of FIG. 1, in which reinforcing joints r are present;

FIG. 4 represents a stent according to the invention made flat, which through a cylindrical coiling enables obtaining the embodiment of FIGS. 1 to 3;

FIG. 4a represents a detailed view of the device of FIG. 4 at the level of a linking arm enabling showing a variant according to which the linking arm can be bent;

Figure 1:
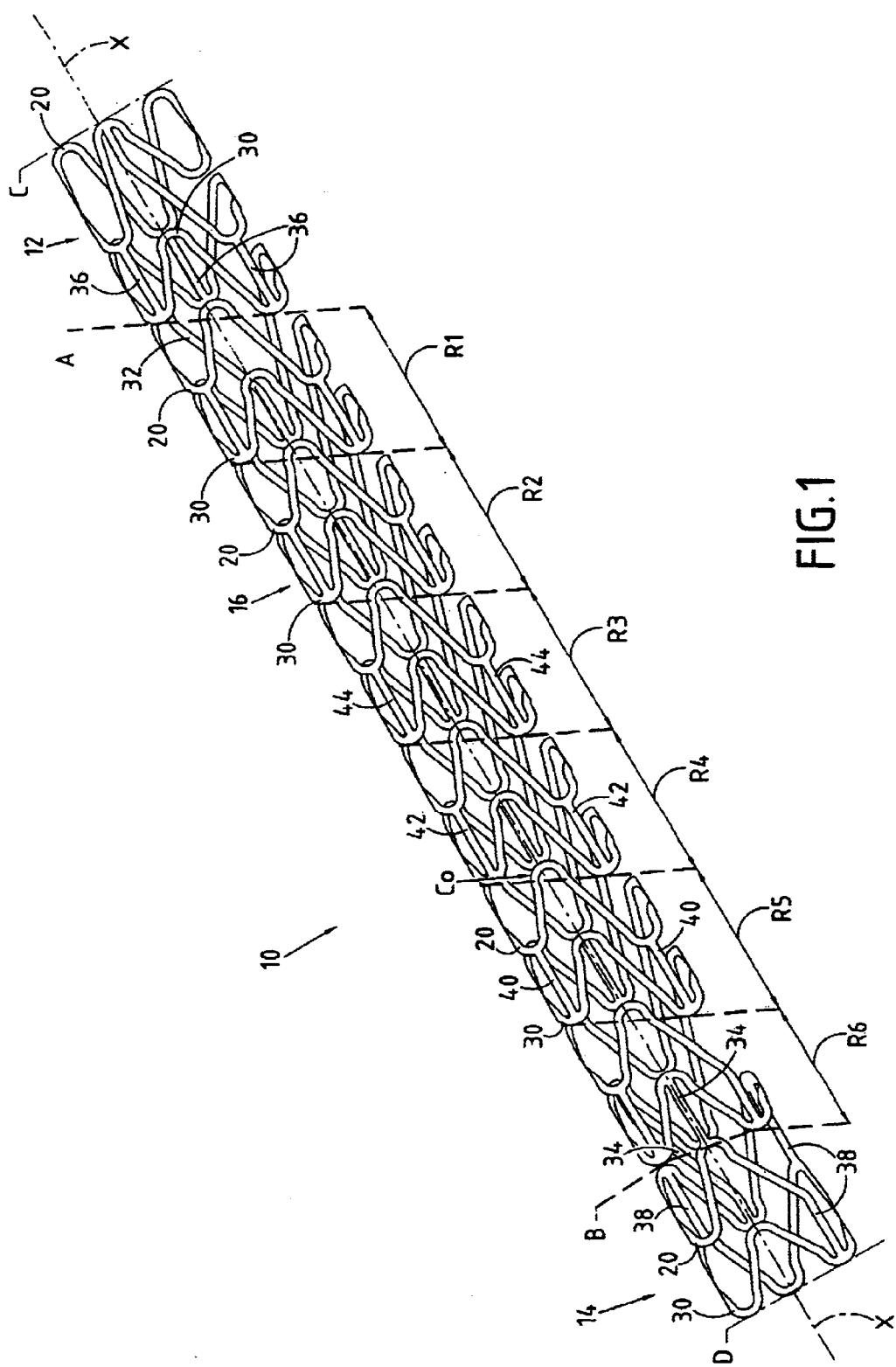
FIG. 1 represents a first currently preferred embodiment of a stent according to the present invention.

FIG. 1 represents a first currently preferred embodiment of a stent forming device, according to the present invention, represented by the general reference number 10. This stent forming device comprises a proximal end portion 12 and a distal end portion 14 which are joined together by a central portion 16.

This stent forming device 10 comprises a first filamentary element 20 spirally coiled at least in the central portion 16.

According to the invention, this device is characterized in that it comprises a second filamentary element 30 spirally coiled at least in the central portion 16, said first and second elements thus defining a double helix structure, as is clearly seen in FIGS. 1 to 8.

Also, within the context of the invention, at least one, preferably both, end portion(s) 12 and 14 are produced with at least one said filamentary element 20 or 30, preferably both, coiled in substantially ring-like fashion. This structure enables reinforcing notably the maintenance of the structure in place and to provide complete covering without overrunning. It is to be noted in FIG. 1 that the dashed straight lines, marked A and B, enable symbolizing the separation between the end portions 12 and 14, and the central portion 16.

According to an advantageous embodiment of the invention, the device 10 comprises end portions 12 and 14 defining respectively a proximal end edge symbolically marked by the straight line C and a distal end edge symbolically marked by the straight line D. The end portions 12 and 14 can be joined to the central portion 16 directly or via at least one joint such as the joint 32 for the end portion 12 and 34 for the end portion 14.

It is to be noted that the end portion 12 and the end portion 14 can be made different, as it appears in FIG. 1. Further, each end portion 12 or 14, can be made with the aid of two filamentary elements coiled in substantially ring-like fashion and joined together by particular linking arms, such as 36, 38, respectively.

Furthermore, in general, the successive linking arms are of various lengths, as is seen also in FIG. 1, in particular in the central portion 16, and will be explained in greater detail in relation to other Figures.

According to another particular embodiment of the invention, the proximal edge C and the distal edge D of the ends are comprised in a plane of substantially circular cross-section, the center of which substantially coincides with the longitudinal axis which is defined by at least the central portion 16 in a double helix.

According to another advantageous variant, the proximal edge C and the distal edge D are comprised in a plane of circular cross-section which is substantially perpendicular to the longitudinal axis X—X which is defined by at least the central portion 16 mentioned above in a double helix, as represented in FIG. 1.

According to another variant of the invention, the proximal edge C and the distal edge D are comprised in a plane of circular cross-section forming an acute angle with the longitudinal axis of the device, of between less than 90° and at least 60°, preferably between less than 90° and at least 70°, as is defined by the embodiment of FIG. 6, which will be explained further on.

It is to be noted that in order to enable a transition between the end portions 12 and 14 and the central portion 16, the end of the end portions has a particular form which ensures the transition between the substantially ring-like end portions and the substantially spiral central portion, which is also visible in FIG. 1.

According to another advantageous embodiment of the invention, the first element 20 and the second filamentary element 30 form a double helix structure and are bent so as to produce a zigzag form, as is represented in FIG. 1, in producing here a spiral zigzag form.

According to a variant enabling a good transversal crossing, the central portion 16 in a double helix comprises at least 3 bends CO defining at least 3 vertices per 360° turn.

In the central portion 16, it will be observed that the first filamentary element 20 and the second filamentary element 30 are joined together by at least some linking arms such as 40, 42, 44 spaced out along said central portion 16.

According to a variant, the double helix is composed of successive 360° turns, hereby referenced $R_1$ to $R_6$ for example, at least some turns comprise at least one linking arm such as 40, 42, 44 between the first element and the second element. Advantageously, each 360° turn comprises at least one linking arm, such as 40, 42, 44.

According to another variant, each turn comprises at least two linking arms, such as 40, 42, 44. In the Example represented, each turn comprises three linking arms.

According to another advantageous variant, at least some linking arms, and in particular each linking arm, at least in the central portion 16, can have at least one bend, as represented in FIG. 4, and this improves the flexibility and the shapability of the device, which is particularly important within the context of stent of long lengths, i.e. of a length of at least 20 mm, which is currently more and more sought after.

According to yet another advantageous embodiment of the invention, the linking arms mentioned above, such as 32, 34, 36, 40, 42, 44 produce a size which is sufficient to enable a sufficient space to be defined between the first and the second spiral elements 20, 30 mentioned above for the passage of a tool in an adjacent canal or canal in which the stent forming device has been disposed. Advantageously, the length of the linking arms such as 40, 42, 44 in the central portion 16 will be identical. The length of the linking arms can be varied within a wide range. Advantageously, the length of the linking arm will be of at least 0.5 mm.

According to a currently preferred variant, the length of linking arm will be of between about 0.5 mm and about 5 mm. In practice, the size will be certainly median between these values.

According to another advantageous embodiment of the invention, the portions of the filamentary element 20 or of the filamentary element 30, which are adjacent to a given bend and therefore defining it, will be of various lengths in the central portion 16 so as to enable defining, at least in part, the spiral pitch sought after. It is understood that at least one portion of this spiral pitch is defined by the inclination of each filamentary element in a turn, as well as the size of the linking arm, such as 40, 42, 44, as is clearly understandable to a person skilled in the art from the geometric structure, as represented in FIG. 1, in considering the turns noted such as $R_1$ to $R_6$.

According to another embodiment of the invention, the straight cross-section of at least one or of the two first and second filamentary elements 20, 30 mentioned above is selected from the group consisting of a straight circular cross-section, a straight polygonal cross-section, such as square, rectangular, pentagonal, hexagonal or octagonal, of a straight polygonal cross-section having rounded edges, such as square having rounded edges or rectangular having rounded edges, or of a straight oval cross-section.

According to another particular embodiment, the size of the straight cross-section of the stent is related directly to the size of the straight cross-section of the canal in which the stent forming device must be inserted.

Furthermore, generally, the diameter of said first element or of said second element, or of both, is of between about one hundredth and about one tenth of the diameter of the straight cross-section of the stent forming device 10 in its initial ready-to-use machining form, as represented in FIG. 1. Advantageously, the diameter of the linking arm will be substantially close to the diameter of the filamentary element, as represented in FIG. 1.

According to an embodiment, the first filamentary element 20 or second filamentary element 30, or both, define a spiral having an inclination with respect to the longitudinal axis, at least of the portion 16, which is defined by the angle α, FIG. 3, of between about 45° and about 80°, advantageously of between about 50° and 70°, currently preferably of about 60°.

According to yet another embodiment of the invention, each bend referenced CO of the filamentary element 20 or 30 has an acute angle which is defined by two successive portions of the filamentary element 20 or 30, of between about 20° and about 60°. As was said above, these successive portions are of various lengths, at least in the central portion 16.

In certain cases, it can be provided for that not all the bends be identical, which can be the case between the end portions 12 and 14 and the central portion 16 and notably in the transition portion between these end portions 12, 14 and the central portion 16.

Naturally, it will be possible to use, as material constituting the stent forming device, any material which is compatible with an implantation in the body of a mammal, preferably man or an animal. Such materials are generally constituted by a biocompatible metal, in particular a medical quality stainless steel, a material having form memory, for example base on an alloy of nickel and titanium.

Figure 2:
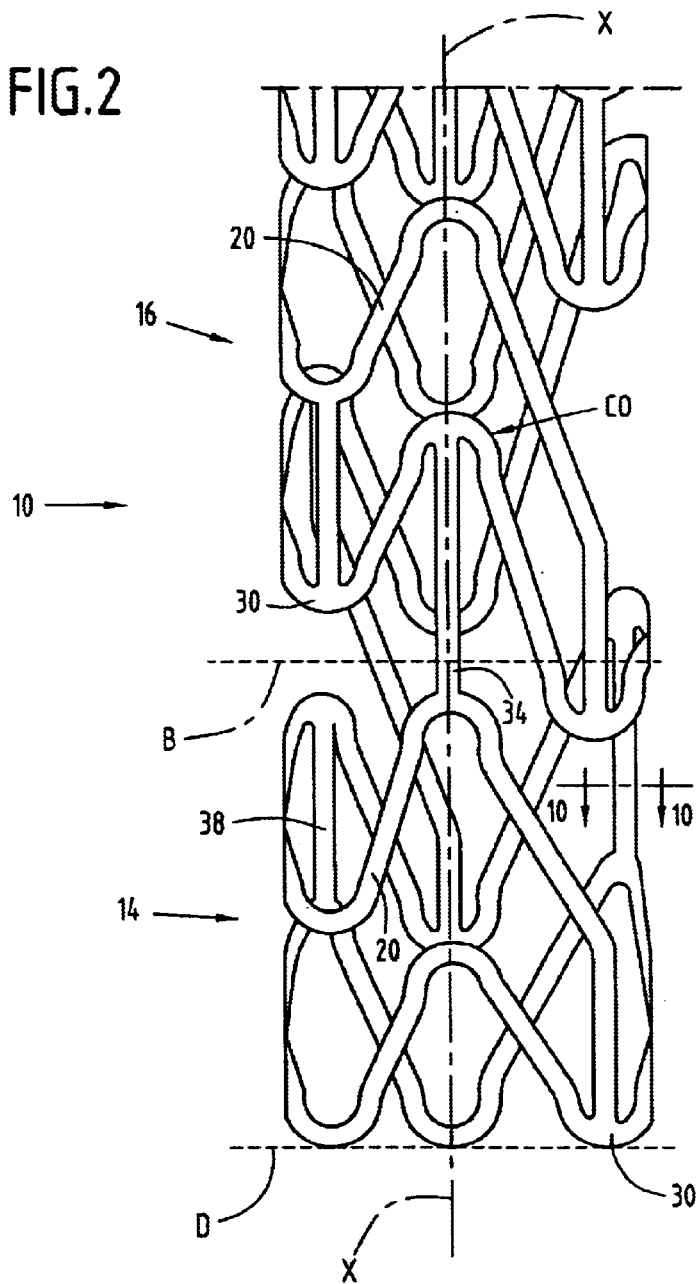
FIG. 2 represents a detailed view of the end, such as the distal end of the device of FIG. 1.
Figure 10:
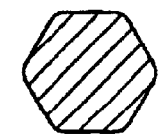
FIG. 10 is a cross-sectional view taken along line 10—10 of FIG. 2, showing a polygonal cross-section modification of the filamentary elements.

FIG. 2 represents a detailed view of an end, such as the distal end 14, and the transition zone at the level of the straight line B with the central portion 16. It is observed that the end portion 14 comprises a first-filamentary element, here preferably constituted by the same filamentary element as the element 20, here partially coiled in ring-like fashion, in order to make the transition zone with the central portion 16, so as to define the distal edge D contained in a plane of circular cross-section which is substantially perpendicular to the longitudinal axis X—X of the stent forming device 10. The end portion 14 comprises also a second filamentary element, which is identical to the second filamentary element 30, which is coiled in the end portion 14 in a ring-like fashion.

In FIG. 3, an enlargement is represented of the central portion 16 in order to visualize the turns better, here $R_3$ to $R_6$, as well as the angle a of inclination of the spiral. In the Example represented in FIGS. 1 and 3, this angle of inclination is of about 62°.

The stent forming device represented in FIGS. 1 to 3 can be obtained from a plate by flat machining, which will be described with reference with FIG. 9, and which gives a developed flat form represented in FIG. 4, before rolling and soldering.

With reference in FIG. 3a, an embodiment is represented which is modified from that of FIG. 3 of the central portion of the embodiment of FIG. 1, according to which at least one reinforcing joint r is provided joining two vertices CO of two successive spiral turns, for example here between the turn $R_4$ and the turn $R_5$. The presence of such a reinforcing joint r can be made only on some spiral turns. The presence of such a reinforcing joint r can be an advantageous solution for reinforcing the hold of the whole and the shoring up strength.

These joints r can be of the number of one or of more per turn, advantageously disposed in a staggered manner with respect to the linking arms 40, 42 or 44.

In FIG. 4, the portions of the proximal 12 and distal 14 ends are clearly seen which are separated substantially by the straight lines A and B of the central portion 16. The same references have been used as in FIG. 1 in order to show the identical portions. From this, the description of the flat element is easily understood from the description, which has been produced for the cylindrical coiled form of FIGS. 1 to 3.

In FIG. 4a, a detailed view is represented of a variant of a linking arm, according to which the linking arm, here 44, has at least one bend 44a, which can be single, or even double, in having in this case a double S form, preferably in the same plane as the elements 20 and 30, as is clearly understandable to a person skilled in the art. This variant enables improving the flexibility, the shapability and the ease of unfolding of the stent forming device, when this bend has a sufficient number of linking arms.

Figure 5:
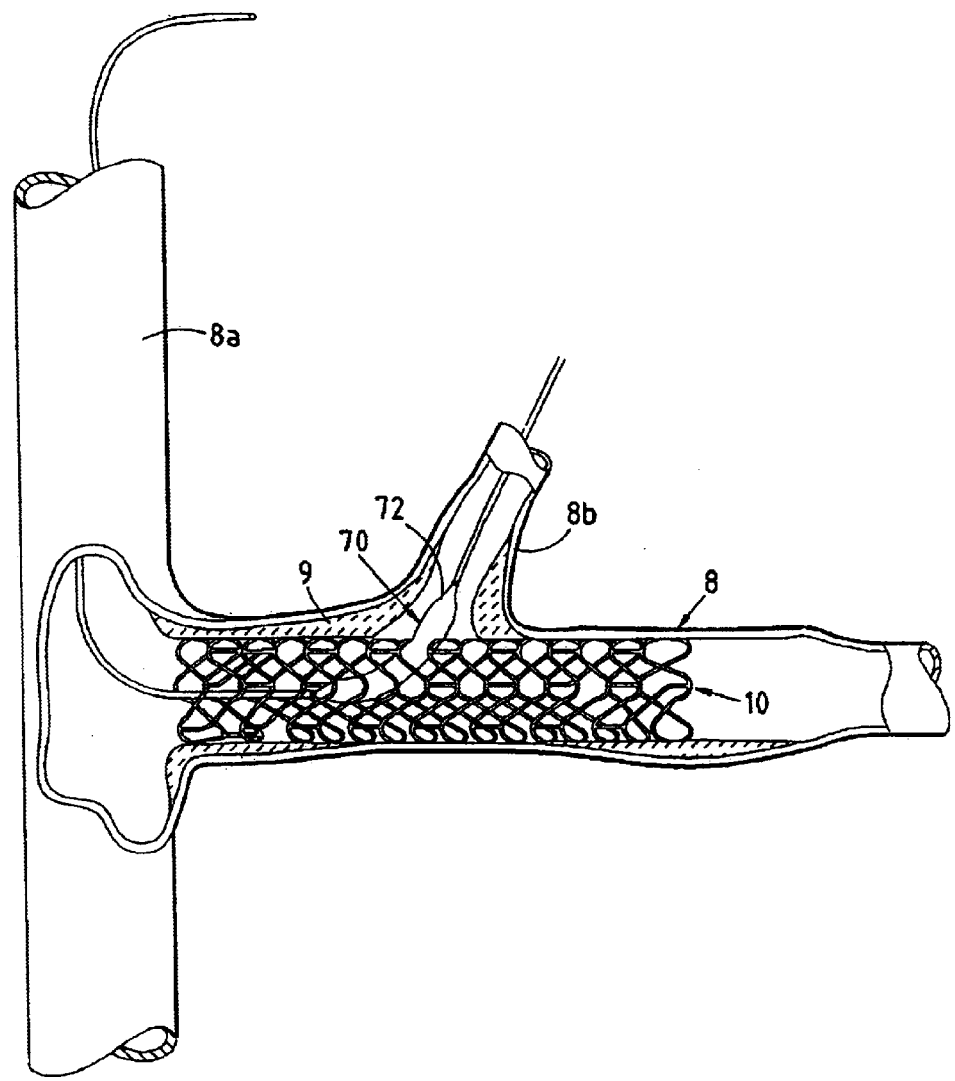
FIG. 5 represents the device of FIGS. 1 to 3 in position in a canal such as an artery.

FIG. 5 represents the stent forming device of the invention 10 according to the present invention in position in a canal 8, such as an artery, which comprises a zone to be treated 9, such as a non-occlusive or occlusive stenosis, which has been pierced. In FIG. 5, the device according to the invention 10 is represented in unfolded form. Within the context of the invention, the radial expansion does not substantially shorten the length of the stent forming device 10, and furthermore maintains the edges of the ends in a plane of substantially circular cross-section, substantially perpendicular to the longitudinal axis X—X of the stent forming device, which coincides here also substantially with the longitudinal axis of the canal in which the device is inserted.

It is seen further in FIG. 5 that the canal 8, such as an artery, is here represented starting at the ostium, in derivation from a bigger canal, here an artery 8a, as well as towards its central portion of a co-lateral canal 8b, such as a straighter artery. It is observed here that the stenosis 9 starts at the ostium and extends beyond the co-lateral canal 8b, which is also initially blocked by the stenosis 9. It is observed that by virtue of the invention, it is possible to carry out a shoring up of the canal 8 at the level of the ostium, without overrunning, by virtue of the ring-like end. Further, it is possible to make an easy crossing of the device laterally in order to enable the passage of another device 70, for example here a balloon device 72, for treating the stenosis at the level of the co-lateral canal 8b.

Figure 6:
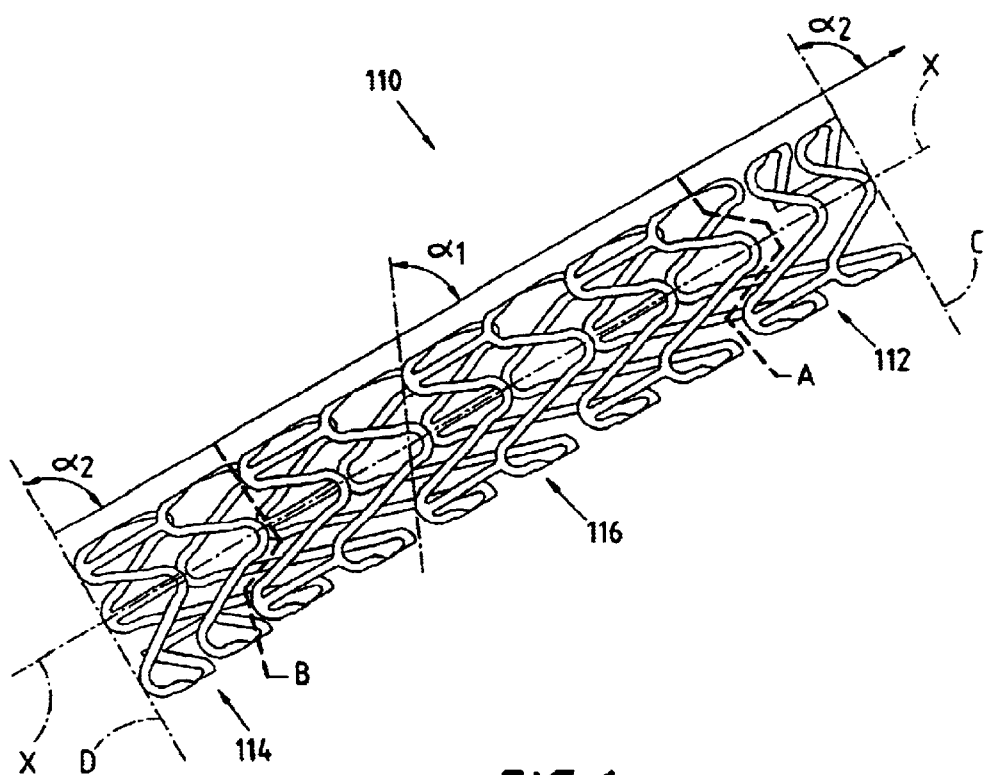
FIG. 6 represents a second embodiment according to the invention with a variable pitch of the spiral.

With reference in FIG. 6, a second embodiment of a stent forming device according to the invention is represented, in the initial non-folded state, represented here by the general reference number 110. From this, the references are increased by 100 in this second embodiment with respect to the embodiment of FIGS. 1 to 3. Thus, this device comprises a first end portion 112 and a second end portion 114 and a central portion 116. In this second embodiment, the pitch of the spiral varies progressively from the central portion 116, in forming an angle of inclination a1, to the end portions 112 and 114, in then forming an angle of inclination a2, in order to lead to the fact that the end portions 112 and 114 produce substantially a ring-like form. At the end portion 112, the residual angle of inclination a2 is represented with respect to the longitudinal axis X—X of the stent forming device. This residual angle a2 will be generally of between less than 90° and at least 60°, preferably between less than 90° and at least 70°. In the embodiment represented in FIG. 6, this angle of inclination which is defined with respect to the longitudinal axis X—X is of the order of 85°, which makes an inclination of about 5° with respect to the perpendicular to the longitudinal axis.

Figure 7:
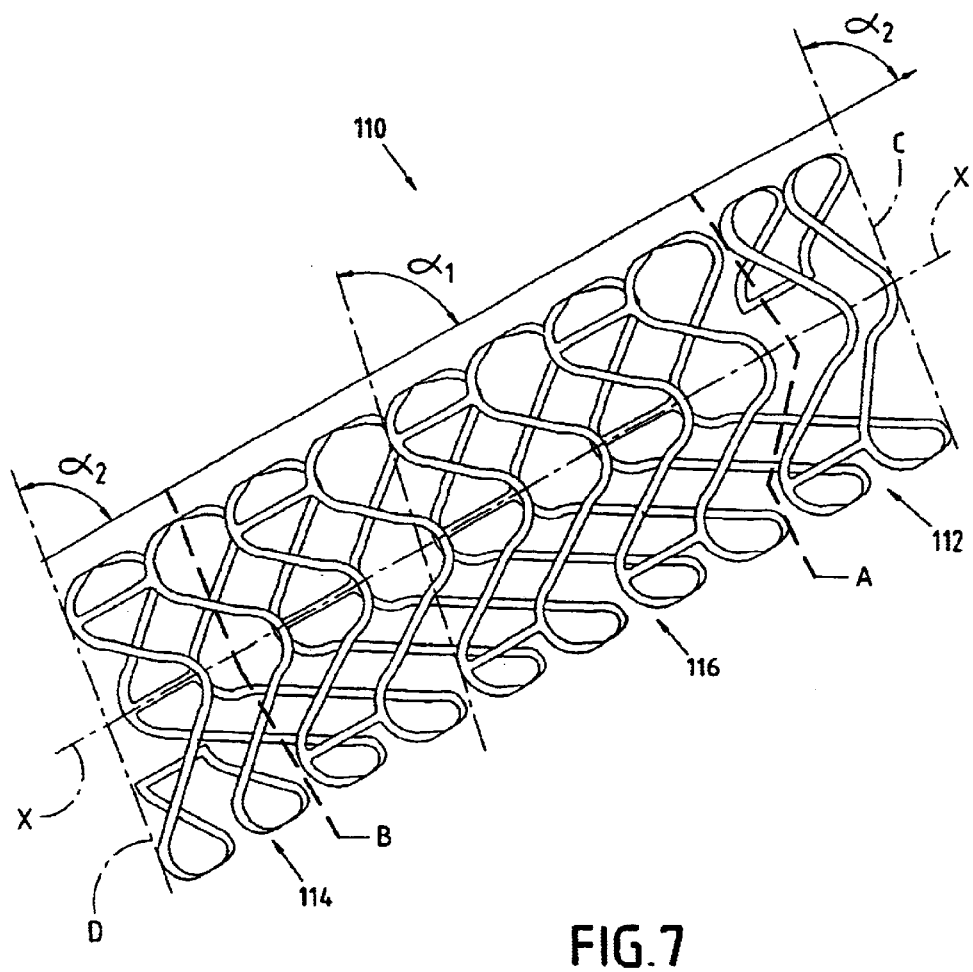
FIG. 7 represents the device of FIG. 6 in the unfolded state.

It will be noted that this embodiment enables always leading to the result of the invention, namely preventing an overrunning at the ends, since the unfolding contributes to increasing the angle of inclination with respect to the longitudinal axis X—X, i.e. to reducing it with respect to the axis which is perpendicular to the longitudinal axis, and this can be observed for a person skilled in the art by the unfolded form of FIG. 7 of the device of FIG. 6.

Figure 8:
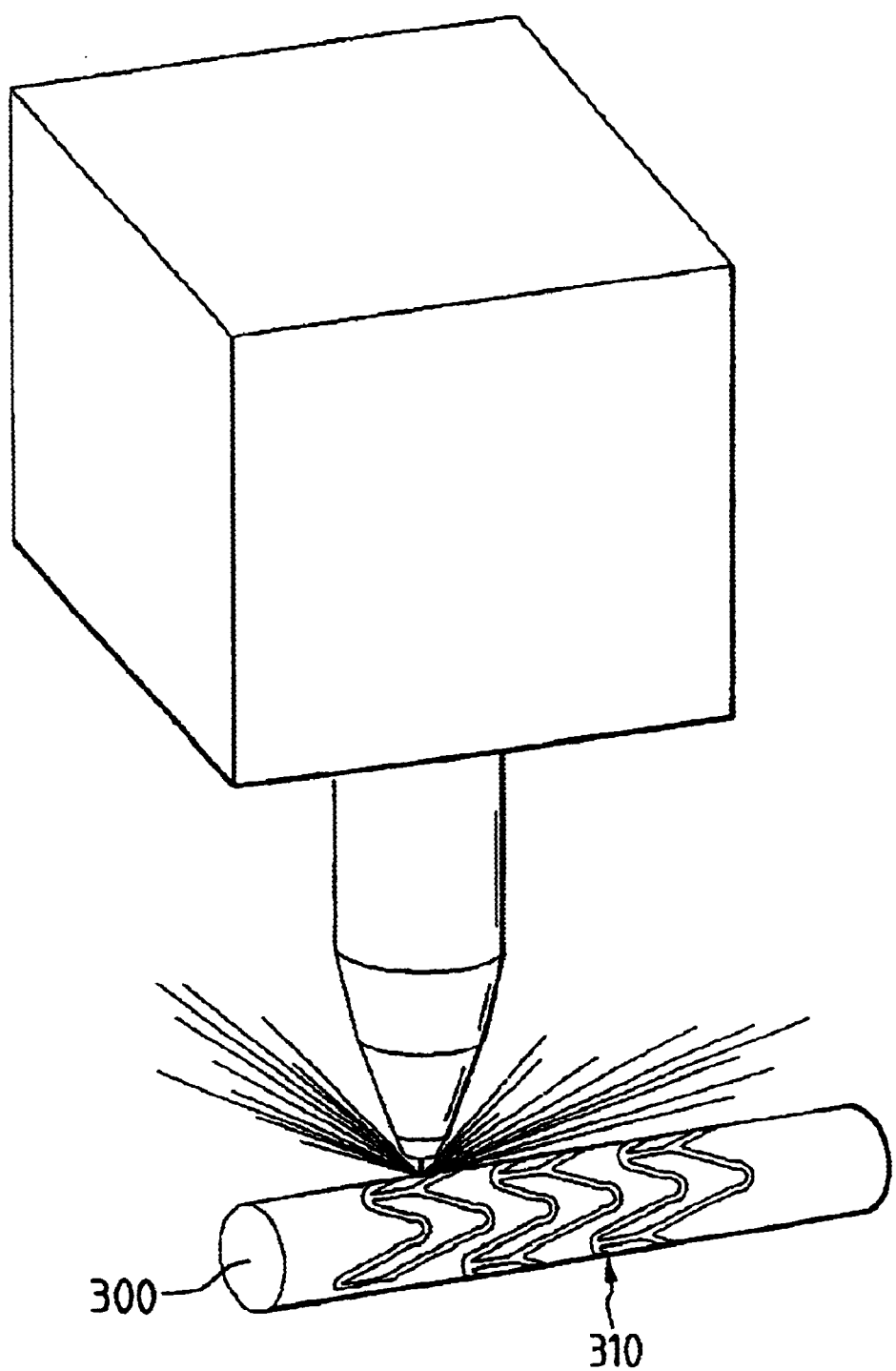
FIG. 8 represents a method of preparation, from a hollow tube having a cylindrical wall, by cutting out.

FIG. 8 represents a method of preparation, from a hallow tube 300 having a full cylindrical wall, by cutting out, which can be made according to several methods, in order to lead to a stent forming device, according to the invention, represented by the general reference number 310. A first method consists in making a laser cut-out, a second method consists in carrying out an electroerosion and a third method consists in carrying out an erosion by jet of a liquid under pressure, in particular by jet of water under pressure of the Karcher® type.

Figure 9:
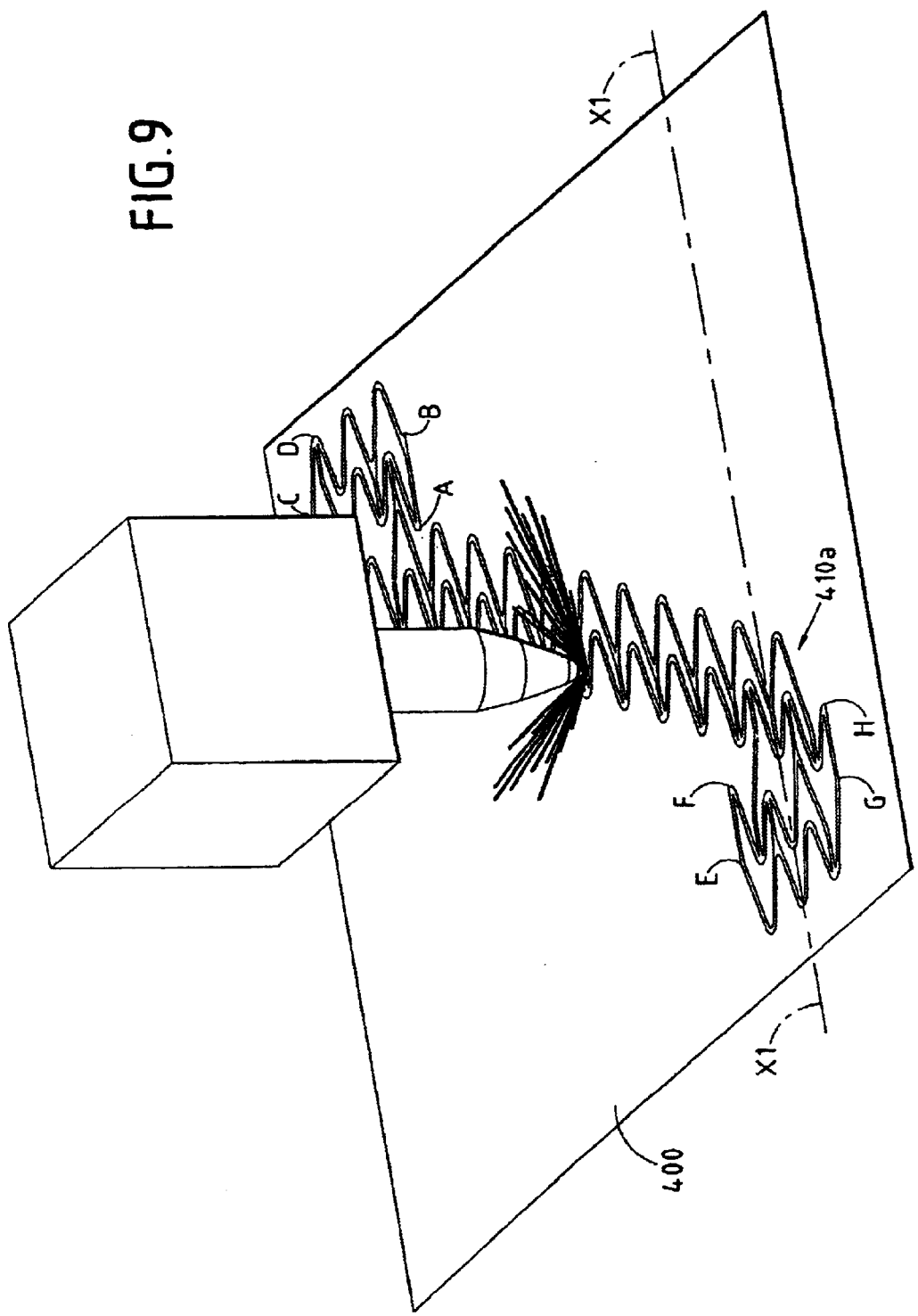
FIG. 9 represents another method of making the device according to the invention by cutting out in a flat element or plate.

FIG. 9 represents another method of preparation, which consists, from a flat element or plate 400, in which the cutting out is made by means of cutting out, which have just been described for FIG. 8, namely laser cutting out, cutting out by electroerosion, or cutting out by a liquid under pressure, in order to obtain a stent forming device represented by the general reference number 410a. In the case of FIG. 9, an element 410a of the type described in FIG. 4 is obtained, and which must be coiled on itself according to the coiling axis X1—X1, and which then enables defining the longitudinal axis X—X of the stent forming device, which is also represented in FIG. 4.

In this embodiment from a flat element, it is understood that the coiling enables bringing the edges AB onto CD and EF onto GH, which are then soldered in order to naturally prevent a re-opening of the system. This embodiment appears to be very practical for a cut-out from a plate, but necessitates a coiling and soldering, which must be prevented in certain cases of application. From this, for other cases, a cut-out is preferred which is from a tube, as described in FIG. 8.

It is understood that the invention gives rise to various embodiments and comprises every means which constitute technical equivalents of the means described and represented. FIGS. 1 to 9 make up an integral part of the present invention and therefore of the present description.

The invention also covers any characteristic which appears novel from the description and from the drawings themselves, with respect to any prior art, and this, as a general means.

It is also understood that it is possible to combine the various embodiments or means of manufacture between themselves. For example, it is possible to make the central portion 16 from a flat element or plate, and the end portions from a hallow tubular element and to combine them together at the moment of assembly.

Within the context of the present invention, the linking arms 40, 42, 44 advantageously join a convex portion of a vertex to a concave portion of another vertex, as represented in the annexed Figures. Generally, in the currently preferred embodiments, the linking arms are provided on a same filamentary element every other bend, but it is understood that this disposition can be modified at will, according to the aim sought after.

What is claimed is:

1. A stent for insertion into a canal in a body comprising a first tubular filamentary element substantially continuously spirally coiled at least in its central portion and having a proximal end portion and a distal end portion; a second tubular filamentary element extending between the proximal and distal end portions and which is substantially continuously spirally coiled at least in its central portion and defining a double helix structure with said first tubular filamentary element, said double helix structure on both ends thereof being ring-shaped to provide increased radial support, and wherein said ends have a plane which is oriented transverse to the longitudinal axis of the stent, the centers of said ring-shaped ends lying along the longitudinal axis of the central portion of the helix structure, and wherein said distal end portion, said proximal end portion and central portion of each element define bends of various lengths.

2. The stent of claim 1, wherein said first filamentary element (20) and said second filamentary element (30) are joined together by a plurality of linking arms spaced out along said central portion.

3. The stent of claim 1, wherein said first and second filamentary elements are bent so as to produce a zigzag form.

4. The stent of claim 1, wherein the double helix comprises successive turns of 360°, at least some turns comprising at least one linking arm between the first element and the second element.

5. The stent of claim 1, wherein the double helix comprises successive turns of 360°, each 360° turn comprising at least one linking arm.

6. The stent of claim 1, wherein the successive spiral turns of each element define bends equal to each other.

7. The stent of claim 1 wherein the length of the linking arms is of the order of at least 0.5 mm.

8. The stent of claim 1 wherein the length of the linking arms is between about 0.5 mm and 5 mm.

9. The stent of claim 1 wherein the central portion comprises at least one reinforcing joint which joins two bends of two successive spiral turns.

10. The stent of claim 1, wherein the central portion comprises one or more reinforcing joints per turn.

11. The stent of claim 1, wherein the cross-section of one or both of said first and second filamentary elements normal to the longitudinal axis of said stent is selected from the group consisting of a circle, a polygon, a polygon having rounded edges and an oval.

12. The stent of claim 11, wherein said polygon is square, rectangular, pentagonal, hexagonal or octagonal.

13. The stent of claim 11, wherein said polygon having rounded edges is a square having rounded edges or rectangular having rounded edges.

14. The stent of claim 2, wherein the linking arm and filamentary elements have substantially equal diameters.

15. The stent of claim 2, wherein the linking arms and the filamentary elements have substantially identical shapes.

16. The stent of claim 1, wherein said first filamentary element, said second filamentary element, or both, define a spiral having an inclination with respect to the longitudinal axis, at least in the central portion, of between 45° and 80°.

17. The stent of claim 1, wherein said first filamentary element, said second filamentary element, or both, define a spiral having an inclination with respect to the longitudinal axis, at least in the central portion, of between 50° and 70°.

18. The stent of claim 1, wherein said first filamentary element, said second filamentary element, or both, define a spiral having an inclination with respect to the longitudinal axis, at least in the central portion, of about 60°.

19. The stent of claim 1, wherein said plane is of circular cross-section and is substantially perpendicular to the longitudinal axis of the stent which is defined by at least the central portion of the helix structure.

20. The stent of claim 1, wherein said plane is of generally circular cross-section and is located at an acute angle of between less than 90° and at least 70° with respect to the longitudinal axis of the helix structure.

21. The stent of claim 2, wherein the linking arms define a space between the first and second spiral elements for the passage of a tool from the interior of the helix structure into the second canal in the body, joining the cabal in which the stent is placed.

22. The stent of claim 1, wherein said first filamentary element (20) and said second filamentary element (30) are joined together by a plurality of linking arms spaced out along said central portion, and wherein the central portion comprises one or more reinforcing joints per turn which are joined in a staggered manner with respect to the linking arms.

23. The stent of claim 1 wherein the double helix structure comprises successive turns of 360°, each 360° turn comprising at least two linking arms and wherein each bend of the filamentary elements have an acute angle which is defined by two successive portions of the respective filamentary element of between about 20° and about 60°.

\* \* \* \* \*